US006808485B2

(12) United States Patent
Zunker

(10) Patent No.: US 6,808,485 B2
(45) Date of Patent: Oct. 26, 2004

(54) COMPRESSIBLE RESILIENT INCONTINENCE INSERT

(75) Inventor: MaryAnn Zunker, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/328,428

(22) Filed: Dec. 23, 2002

(65) Prior Publication Data

US 2004/0122285 A1 Jun. 24, 2004

(51) Int. Cl.[7] .......................... A61F 2/00; A61M 31/00
(52) U.S. Cl. .................................. 600/29; 604/515
(58) Field of Search ......................... 600/29, 32, 30; 604/515, 279, 517, 544, 329, 330, 500, 11–18, 57, 59, 60, 385.17, 904, 385.1; 128/885, DIG. 25, 830–841

(56) References Cited

U.S. PATENT DOCUMENTS

| 1,280,979 | A | 10/1918 | Ellis |
| 1,790,801 | A | 2/1931 | Dickstein |
| 2,057,206 | A | 10/1936 | Pohl |
| 2,092,427 | A | 9/1937 | Ross |
| 2,201,412 | A | 5/1940 | Stein |
| 2,264,586 | A | 12/1941 | Ross |
| 2,298,752 | A | 10/1942 | Crockford |
| 2,355,628 | A | 8/1944 | Calhoun |
| 2,401,585 | A | 6/1946 | Seidler |
| 2,487,200 | A | 11/1949 | Trager |

(List continued on next page.)

FOREIGN PATENT DOCUMENTS

| BR | PI 9302334-0 A | 7/1995 |
| DE | 1815375 | 9/1970 |
| DE | 2747245 | 4/1979 |
| DE | 3122954 A1 | 1/1983 |
| DE | 3720858 A1 | 1/1989 |

(List continued on next page.)

OTHER PUBLICATIONS

U.S. patent application No. 09/675,459 filed Sep. 28, 2000, entitled "Urinary Incontinence Device and Method of Making Same" pp. 1–24.
U.S. patent application No. 09/675,460 filed Sep. 28, 2000, entitled "Resilient Incontinence Insert and a Method of Making the Same", pp. 1–29.
U.S. patent application No. 10/039,230 filed Dec. 31, 2001, entitled "Incontinence Insert Device and Method of Using Same", pp. 1–18.
U.S. patent application filed Mar. 26, 2002, entitled "Absorbent Article Having a Multilayer Blended Core and a Method of Forming" pp. 1–26.
U.S. patent application filed May 23, 2002, entitled "Absorbent Article Having a Multi–Layer Absorbent Structure", pp. 1–50.
U.S. patent application No. 10/245,964 filed Sep. 18, 2002, entitled "Molar Shaped Vaginal Incontinence Insert", pp. 1–16.
U.S. patent application No. 10/246,005 filed Sep. 18, 2002, entitled "C–Shaped Vaginal Insert Incontinence Device", pp. 1–15.
Concert Fabricatation, Ltee, *Nonwovens Industry*, p. 1110, May, 1996.

*Primary Examiner*—Eric F. Winakur
*Assistant Examiner*—Nikita R. Veniaminov
(74) *Attorney, Agent, or Firm*—Brinks Hofer Gilson & Lione; G. Peter Nichols

(57) ABSTRACT

A urinary incontinence device is disclosed. The device is a compressible resilient insert having top that contacts at least two opposed vaginal walls and deforms and substantially conforms to the shape of the vaginal cavity or cervical fornices. A removal member may be provided on the device such that when the removal member is pulled the device is removed from the vagina.

21 Claims, 3 Drawing Sheets

U.S. PATENT DOCUMENTS

| | | |
|---|---|---|
| 2,491,017 A | 12/1949 | Robinson |
| 2,501,972 A | 3/1950 | Seidler |
| 2,519,912 A | 8/1950 | Laun |
| 2,700,188 A | 1/1955 | Buresh et al. |
| 2,711,173 A | 6/1955 | Seidler |
| 2,739,593 A | 3/1956 | McLaughlin |
| 2,890,497 A | 6/1959 | Langdon et al. |
| 2,938,519 A | 5/1960 | Marco |
| 3,011,495 A | 12/1961 | Brecht |
| 3,032,036 A | 5/1962 | Rader et al. |
| 3,034,508 A | 5/1962 | Nalle, Jr. |
| 3,079,921 A | 3/1963 | Brecht et al. |
| 3,090,385 A | 5/1963 | Brecht |
| 3,138,159 A | 6/1964 | Schmidt |
| 3,369,544 A | 2/1968 | Crockford |
| 3,409,011 A | 11/1968 | Mittag |
| 3,452,752 A | 7/1969 | Crescenzo |
| 3,469,286 A | 9/1969 | Crockford |
| 3,543,754 A | 12/1970 | Jones, Sr. |
| 3,554,184 A | 1/1971 | Habib |
| 3,596,328 A | 8/1971 | Voss |
| 3,643,661 A | 2/1972 | Crockford |
| 3,644,078 A | 2/1972 | Tachibana et al. |
| 3,646,929 A | 3/1972 | Bonnar |
| 3,705,575 A | 12/1972 | Edwards |
| 3,706,311 A | 12/1972 | Kokx et al. |
| 3,762,413 A | 10/1973 | Hanke |
| 3,765,417 A | 10/1973 | Crockford |
| 3,799,165 A | 3/1974 | Wennerblom et al. |
| 3,866,613 A | 2/1975 | Kenny et al. |
| 3,886,629 A | 6/1975 | Nakai et al. |
| 3,918,452 A | 11/1975 | Cornfield |
| 3,971,378 A | 7/1976 | Krantz |
| 3,983,875 A | 10/1976 | Truman |
| 4,011,034 A | 3/1977 | Curry et al. |
| 4,019,498 A | 4/1977 | Hawtrey et al. |
| 4,060,360 A | 11/1977 | Tapp |
| 4,074,393 A | 2/1978 | Hicklin et al. |
| 4,139,006 A | 2/1979 | Corey |
| 4,144,619 A | 3/1979 | White et al. |
| 4,148,317 A | 4/1979 | Loyer |
| 4,160,004 A | 7/1979 | Curry et al. |
| 4,160,059 A | 7/1979 | Samejima |
| 4,212,301 A | 7/1980 | Johnson |
| 4,261,340 A | 4/1981 | Baumel et al. |
| 4,266,546 A | 5/1981 | Roland et al. |
| 4,307,716 A | 12/1981 | Davis |
| 4,318,407 A | 3/1982 | Woon |
| 4,335,721 A | 6/1982 | Matthews |
| 4,359,357 A | 11/1982 | Friese |
| 4,398,532 A | 8/1983 | Sweeney, III |
| 4,486,191 A | 12/1984 | Jacob |
| 4,494,278 A | 1/1985 | Kroyer et al. |
| 4,498,899 A | 2/1985 | Gross |
| 4,516,570 A | 5/1985 | Taban |
| 4,536,178 A | 8/1985 | Lichstein et al. |
| 4,573,963 A | 3/1986 | Sheldon |
| 4,573,964 A | 3/1986 | Huffman |
| 4,668,557 A | 5/1987 | Lakes |
| 4,669,478 A | 6/1987 | Robertson |
| 4,823,814 A | 4/1989 | Drogendijk et al. |
| 4,857,044 A | 8/1989 | Lennon |
| 4,875,898 A | 10/1989 | Eakin |
| 4,920,986 A | 5/1990 | Biswas |
| 4,921,474 A | 5/1990 | Suzuki et al. |
| 4,950,264 A | 8/1990 | Osborn, III |
| 4,973,302 A | 11/1990 | Armour et al. |
| 5,007,894 A | 4/1991 | Enhorning |
| 5,009,653 A | 4/1991 | Osborn, III |
| 5,036,867 A | 8/1991 | Biswas |
| 5,041,077 A | 8/1991 | Kulick |
| 5,045,079 A | 9/1991 | West |
| 5,074,855 A | 12/1991 | Rosenbluth et al. |
| 5,080,659 A | 1/1992 | Nakanishi |
| 5,112,348 A | 5/1992 | Glassman |
| 5,147,301 A | 9/1992 | Ruvio |
| 5,188,624 A | 2/1993 | Young, Sr. et al. |
| 5,224,494 A | 7/1993 | Enhorning |
| 5,273,521 A | 12/1993 | Peiler et al. |
| 5,336,208 A | 8/1994 | Rosenbluth et al. |
| 5,352,182 A | 10/1994 | Kalb et al. |
| 5,355,896 A | 10/1994 | Schulman |
| 5,383,869 A | 1/1995 | Osborn, III |
| 5,386,836 A | 2/1995 | Biswas |
| 5,395,308 A | 3/1995 | Fox et al. |
| 5,395,309 A | 3/1995 | Tanaka et al. |
| 5,476,434 A | 12/1995 | Kalb et al. |
| 5,483,976 A | 1/1996 | McLaughlin et al. |
| 5,498,478 A | 3/1996 | Hansen et al. |
| 5,512,032 A | 4/1996 | Kulisz et al. |
| 5,533,990 A | 7/1996 | Yeo |
| 5,545,179 A | 8/1996 | Williamson, IV |
| 5,554,109 A | 9/1996 | Frayman |
| 5,603,685 A | 2/1997 | Tutrone, Jr. |
| 5,609,559 A | 3/1997 | Weitzner |
| 5,609,586 A | 3/1997 | Zadini et al. |
| 5,611,768 A | 3/1997 | Tutrone, Jr. |
| 5,613,961 A | 3/1997 | DiPalma et al. |
| 5,618,256 A | 4/1997 | Reimer |
| 5,624,423 A | 4/1997 | Anjur et al. |
| 5,649,916 A | 7/1997 | DiPalma et al. |
| 5,659,934 A | 8/1997 | Jessup et al. |
| 5,752,525 A | 5/1998 | Simon et al. |
| 5,755,906 A | 5/1998 | Achter et al. |
| 5,771,899 A | 6/1998 | Martelly et al. |
| 5,785,640 A | 7/1998 | Kresch et al. |
| 5,795,346 A | 8/1998 | Achter et al. |
| 5,807,372 A | 9/1998 | Balzar |
| 5,813,973 A | 9/1998 | Gloth |
| 5,816,248 A | 10/1998 | Anderson et al. |
| 5,849,000 A | 12/1998 | Anjur et al. |
| 5,873,971 A | 2/1999 | Balzar |
| 5,885,204 A | 3/1999 | Vergano |
| 5,894,842 A | 4/1999 | Rabin et al. |
| 5,908,379 A | 6/1999 | Schaefer et al. |
| 5,948,829 A | 9/1999 | Wallajapet et al. |
| 5,985,434 A | 11/1999 | Qin et al. |
| 5,988,169 A | 11/1999 | Anderson et al. |
| 5,988,386 A | 11/1999 | Morrow |
| 6,019,743 A | 2/2000 | Cole et al. |
| 6,030,375 A | 2/2000 | Anderson et al. |
| 6,039,716 A | 3/2000 | Jessup et al. |
| 6,039,828 A | 3/2000 | Achter et al. |
| 6,056,714 A | 5/2000 | McNelis et al. |
| 6,071,259 A | 6/2000 | Steiger et al. |
| 6,090,038 A | 7/2000 | Zunker et al. |
| 6,090,098 A | 7/2000 | Zunker et al. |
| 6,095,998 A | 8/2000 | Osborn, III et al. |
| 6,127,594 A | 10/2000 | Rosseland |
| 6,142,928 A | 11/2000 | Zunker et al. |
| 6,189,535 B1 | 2/2001 | Enhorning |
| 6,207,099 B1 | 3/2001 | Rooyakkers et al. |
| 6,214,274 B1 | 4/2001 | Melius et al. |
| 6,248,089 B1 | 6/2001 | Porat |
| 6,267,575 B1 | 7/2001 | Rooyakkers et al. |
| 6,270,470 B1 | 8/2001 | Buck et al. |
| 6,283,952 B1 | 9/2001 | Child et al. |
| 6,323,388 B1 | 11/2001 | Melius et al. |
| 6,340,411 B1 | 1/2002 | Hansen et al. |
| 6,383,960 B1 | 5/2002 | Everett et al. |
| 6,415,484 B1 | 7/2002 | Moser |

| | | |
|---|---|---|
| 6,419,777 B1 | 7/2002 | Achter et al. |
| 6,420,626 B1 | 7/2002 | Erspamer et al. |
| 6,425,979 B1 | 7/2002 | Hansen et al. |
| 6,558,370 B2 | 5/2003 | Moser |
| 6,645,136 B1 | 11/2003 | Zunker et al. |
| 2002/0083949 A1 | 7/2002 | James |
| 2002/0090390 A1 | 7/2002 | Mahashabde et al. |
| 2002/0156441 A1 | 10/2002 | Sawyer et al. |
| 2002/0169428 A1 | 11/2002 | Fell et al. |

FOREIGN PATENT DOCUMENTS

| | | |
|---|---|---|
| DE | 19602878 C1 | 1/1996 |
| EP | 0460807 A2 | 12/1991 |
| EP | 0264258 B1 | 4/1992 |
| EP | 0498912 A1 | 8/1992 |
| EP | 0 663 197 A | 7/1995 |
| EP | 0663197 A1 | 7/1995 |
| EP | 0363421 B2 | 10/1995 |
| EP | 0714271 B1 | 6/1996 |
| FR | 2228464 | 12/1974 |
| FR | 2342717 | 9/1977 |
| GB | 1115727 | 5/1968 |
| GB | 1116742 | 6/1968 |
| GB | 1359343 | 7/1974 |
| GB | 2 364 645 A | 2/2002 |
| WO | WO 88/10106 | 12/1988 |
| WO | WO 94/13223 | 6/1994 |
| WO | WO 95/05790 | 3/1995 |
| WO | WO 95/16423 | 6/1995 |
| WO | WO 95/28139 | 10/1995 |
| WO | WO 96/10965 | 4/1996 |
| WO | WO 97/36642 A1 | 10/1997 |
| WO | WO 98/06365 | 2/1998 |
| WO | WO 98/24392 | 6/1998 |
| WO | WO 98/42281 | 10/1998 |
| WO | WO 98/51251 | 11/1998 |
| WO | WO 00/36996 | 6/2000 |
| WO | WO 00/37012 | 6/2000 |
| WO | WO 00/37013 | 6/2000 |
| WO | WO 00/41882 | 7/2000 |
| WO | WO 00/74620 A1 | 12/2000 |
| WO | WO 01/12119 A1 | 2/2001 |
| WO | WO 01/35886 A1 | 5/2001 |
| WO | WO 01/54641 A1 | 8/2001 |
| WO | WO 02/26173 A | 4/2002 |
| WO | WO 02/053071 A1 | 7/2002 |
| WO | WO 02/056812 A2 | 7/2002 |
| WO | WO 02/069868 A1 | 9/2002 |
| WO | WO 02/069871 A1 | 9/2002 |
| WO | WO 02/080834 A2 | 10/2002 |
| WO | WO 02/089704 A2 | 11/2002 |
| WO | WO 02/098323 A1 | 12/2002 |

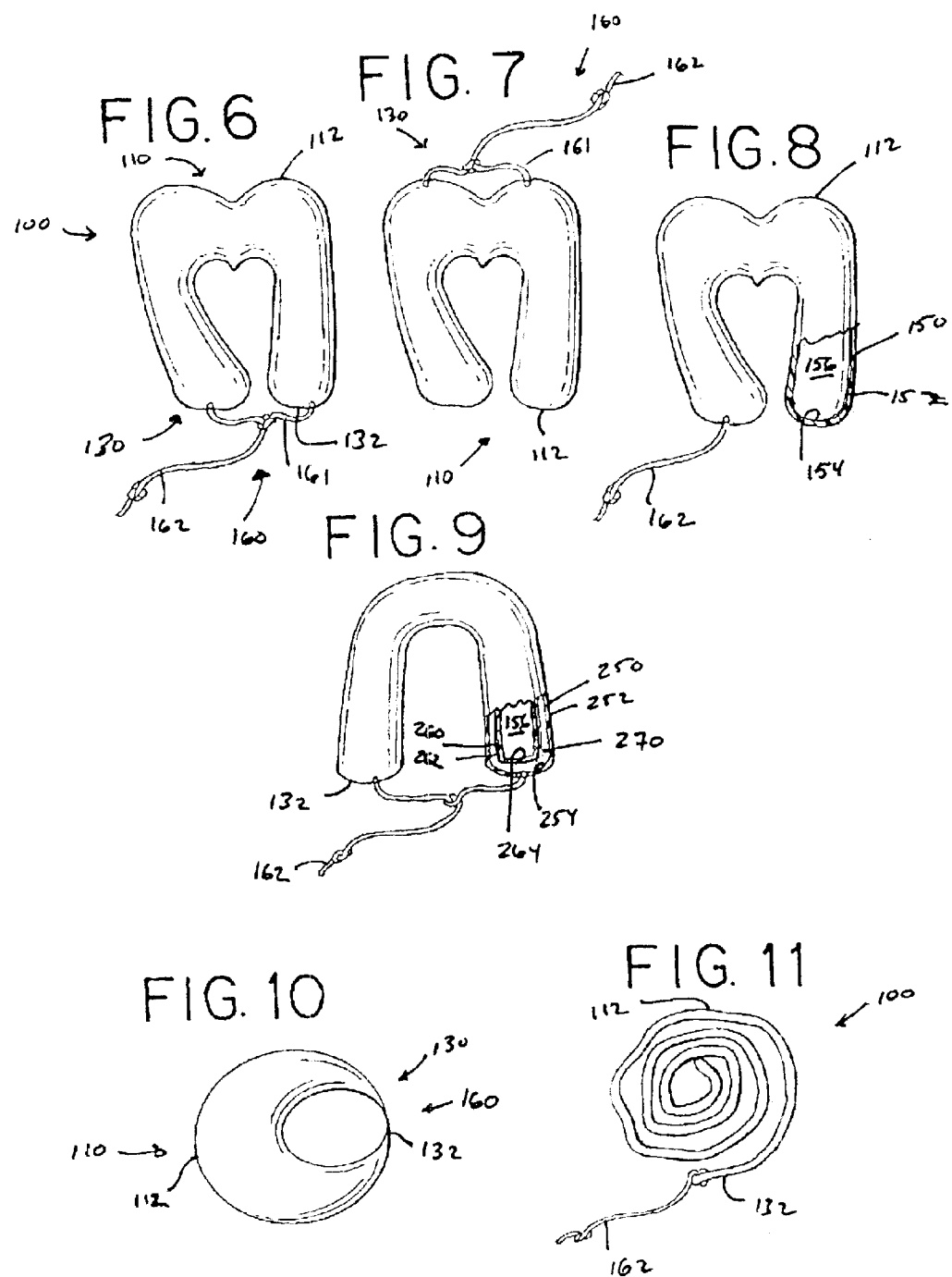

COMPRESSIBLE RESILIENT INCONTINENCE INSERT

FIELD OF THE INVENTION

The present invention relates to a urinary incontinence device and a method of using the same. More specifically, this invention relates to a compressible resilient device for alleviating female urinary incontinence, particularly during episodes of increased intra-abdominal pressure.

BACKGROUND OF THE INVENTION

The primary etiological factor producing genuine stress urinary incontinence is the incomplete transmission of abdominal pressure to the proximal urethra due to displacement from its intra-abdominal position. Some women, especially women who have given birth to one or more children, older women, and women who have experienced rapid weight gain, are overweight or obese can experience incidences of involuntary urine loss due to stress urinary incontinence or combined stress and urge incontinence. A sneeze or cough increases the intra-abdominal pressure which in turn increases the pressure on a person's bladder causing the involuntary release of urine. The frequency and severity of such urine loss can increase as the muscles and tissues near the urethro-vaginal myofascial area grow weaker. It has also been recognized that the urinary sphincter muscle, which is located at the upper end of the urethra, adjacent to the bladder, works well at sealing off the passing of urine from the bladder to the urethra when it has a round or circular cross-sectional configuration.

Support of the proximal urethra elevates it above the pelvic floor and subjects it to increases in intra-abdominal pressure, thus allowing compression of the urethra and maintenance of continence. When this passageway becomes distorted into a cross-sectional configuration having more of an elliptical or oval appearance, however, the sphincter muscle can not close properly. Therefore, the tendency for involuntary urine loss increases. One must remember that the urethra and vagina are not separate structures. Because of their common derivation from the urogenital sinus, they are fused in the distal two-thirds of the urethra. In this region they are bound together by the endopelvic connective tissue so that the support of the urethra depends not only on the attachments of the urethra itself to adjacent structures but also on the connection of the vagina and periurethral tissues to the pelvic wall.

With increasing numbers of females experiencing incontinence, there is an ever-increasing need for a non-surgical method or measure to reduce the involuntary urine loss. Although there are specialized products available for this purpose, most can only be purchased with a prescription and they need to be properly sized, physically inserted and/or adjusted by a medical doctor for them to correctly perform.

In view of the lack of non-prescription, commercially available devices, there is a need for a urinary incontinence device that can be purchased by the consumer and that is uncomplicated and user friendly. Furthermore, there is a need for a urinary incontinence device that is easy for a woman to insert into and remove from their body that is more comfortable to wear and to provide psychological and realistic assurance that it is capable of properly performing over an extended period of time.

SUMMARY OF THE INVENTION

The present invention relates to an intra-vaginal urinary incontinence device that is a compressible resilient insert. The insert has a top and a bottom. In use, at least a portion of the top respectively contacts at least the anterior and posterior vaginal walls and may also simultaneously contact the left and right vaginal walls to restore the retropubic position of the bladder neck. It may also contact the anterior and/or posterior cervical formices.

The top of the insert is provided with a top surface that may be closed or may be provided with a passageway. Likewise, the bottom of the insert may be closed or may be provided with a passageway. When a passageway is present on the top surface, a passageway is provided on the bottom surface and the passageway on the top surface communicates with the passageway provided on the bottom surface to allow fluids to pass through the insert. In one embodiment, a channel is provided to connect the passageway provided on the top surface with the passageway provided on the bottom surface.

The insert may also be provided with a removal member that cooperates with the insert to allow the insert to be removed from the vagina. The removal member may be separate from or integral with the insert. Accordingly, in one embodiment, the removal member is attached to at least a portion of the bottom of the insert. Alternatively, the removal member is attached to at least a portion of the top of the insert.

The insert may be formed from a variety of biocompatible materials and may be formed as a solid or semi-solid mass of a compressible, resilient, biocompatible material that allows the insert to deform and to substantially conform to the shape of the object deforming the insert. Alternatively, the insert may be formed such that the insert has a thin wall that defines an outer surface and an inner surface. In this embodiment, the inner surface defines an interior of the insert. The interior of the insert may contain a compressible resilient material that allows the wall of the insert to deform and substantially conform to the shape of the object acting to deform the wall such as one or more of the vaginal walls.

In another embodiment, the insert may be formed from an inner wall spaced from an outer wall to define a plenum. The plenum may be filled with a compressible resilient material, normal saline solution, aqueous gel, mineral gel, biocompatible materials selected from biocompatible plastics, silicones, polyurethane, gels, air or other gas. In addition, the inner wall defines an interior of the insert. The interior may be filled with air or other gas or it may be filled with a compressible resilient material that may be the same as or different from the compressible resilient material that is present in the plenum, if such a material is present in the plenum. It may also contain a medicament or drug for immediate or prolonged therapeutic effect.

Put another way, the device of the present invention is an intra-vaginal device that can simultaneously engage the anterior vaginal wall and the posterior vaginal wall, or each of the anterior vaginal wall, the posterior vaginal wall, the left vaginal wall and the right vaginal wall. It may also contact the anterior and/or posterior cervical formices. The device provides anatomical realignment of the urethra and sphincter muscles to restore the retropubic position of the bladder neck so intra-abdominal pressure is once again transmitted equally to the bladder and urethra. The device is formed of a compressible resilient material so that, in use, it may be resiliently deformed to conform to the shape of the vaginal walls.

The present invention also includes a method of alleviating female urinary incontinence by providing a female urinary incontinence device as described above and in the specification below, selectively inserting the device into a woman's vagina so that the device simultaneously contacts or the anterior vaginal wall and the posterior vaginal wall. It may also contact the anterior and/or posterior cervical formices. Alternatively, it may contact all the walls in the bladder neck region to restore the retropubic position of the bladder neck.

Advantageously, the device and method of present invention provides for control of female urinary incontinence by use of a device that does not create undue friction or distension of the mucosal tissue and yet allows for normal discharge of vaginal secretions.

BRIEF DESCRIPTION OF THE DRAWINGS

FIG. 6 is front view of one embodiment of the urinary incontinence device of the present invention that is in an M-shape and having a removal member attached to each of the legs of the device.

FIG. 7 is a front view of one embodiment of the urinary incontinence device of the present invention that is in an M-shape and having a removal member attached to the portion of the device forming the top of the M.

FIG. 8 is a front view of one embodiment of the urinary incontinence device of the present invention that is in an M-shape and having a removal member attached to one of the legs of the device.

FIG. 9 is front view of one embodiment of the urinary incontinence device of the present invention that is in an inverted U-shape or arch and having a removal member attached to each of the legs of the device. The urinary incontinence device is also illustrated as having outer wall and an inner wall to define a plenum that may be filled.

FIG. 10 is a side view of another embodiment of the urinary incontinence device of the present invention having an out-of-round or oval shape (as shown here).

FIG. 11 is a top view of another embodiment of the urinary incontinence device of the present invention having a spiral shape.

DESCRIPTION OF THE INVENTION

Figure 1:
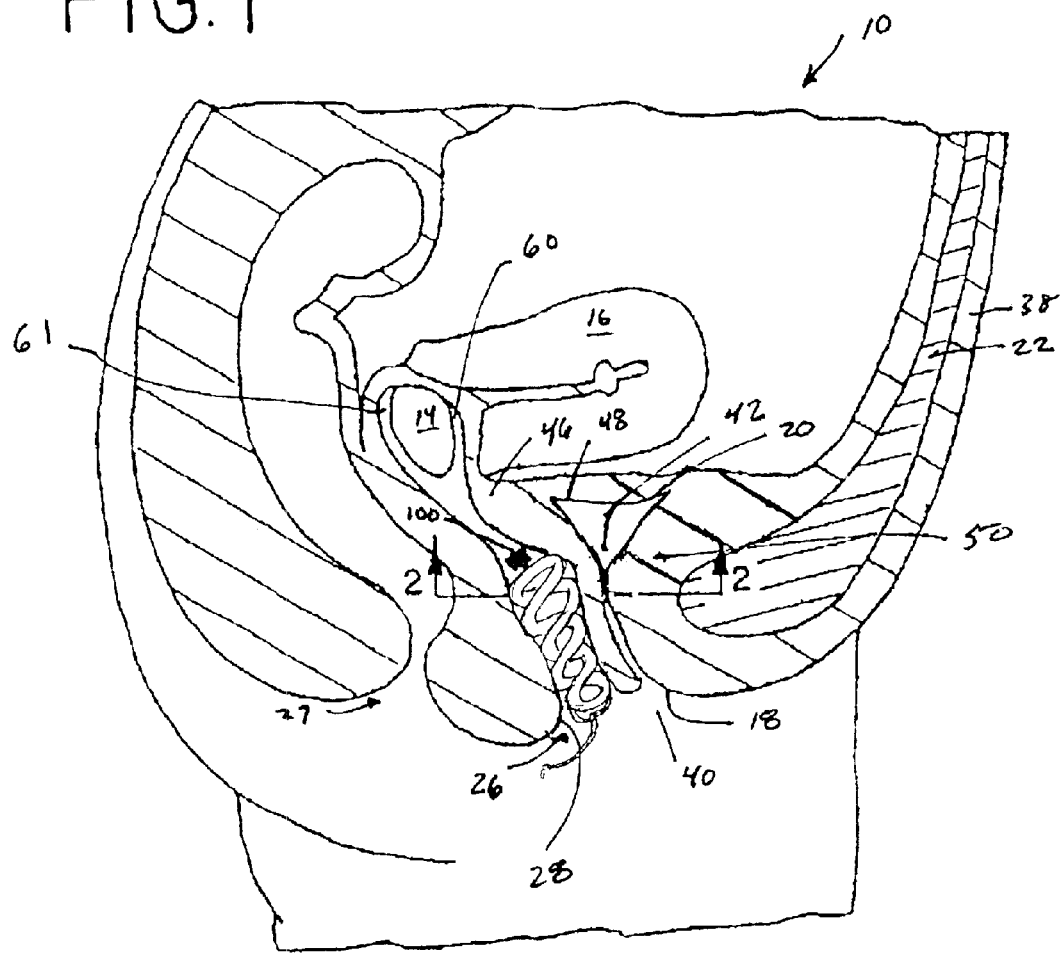
FIG. 1 is a mid-sagittal section of a human torso showing one embodiment of a urinary incontinence device according to the present invention positioned in the vaginal canal showing the device aligned with the bladder neck region to elevate and support the bladder and to cooperate with the symphysis pubis to allow the urethral tube to be compressed upon itself and alleviate urinary incontinence during episodes of increased intra-abdominal pressure.

Turning now to FIG. 1, a human torso 10 of a female is shown with a vagina 12, a cervix 14, a uterus 16, a urethra 18, a bladder 20 and a symphysis pubis 22. The vagina 12 has an introital opening 24 that exits the human body 10 and contains a vaginal canal 26 that extends from the introital opening 24 to the cervix 14. The vaginal canal 26 has a length that ranges from between about 4 inches to about 6 inches (about 102 millimeters (mm), to about 153 mm) in most women. The cervix 14 is the entrance to the womb and is located between the upper aspect of the vaginal canal 26 and the uterus 16. The rectum 27 is located posterior to the vagina 12. The vaginal canal 26 has an inner periphery 28.

Figure 2:
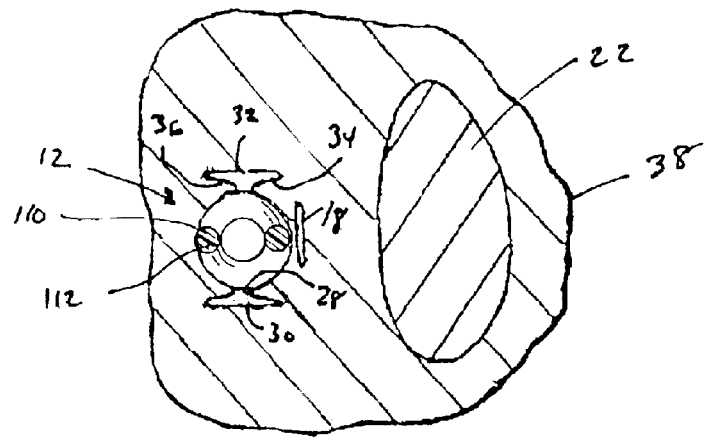
FIG. 2 is a sectional view taken along line 2—2 of FIG. 1 wherein the device circumferentially contacts the anterior vaginal wall and the posterior vaginal wall.

As best seen in FIG. 2, the inner periphery 28 of the vagina is made up of a right lateral wall 30, a left lateral wall 32, an anterior wall 34, and a posterior wall 36. The four walls 30, 32, 34, and 36 encompass the entire 360 degrees of the inner periphery 28. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is the most important section for alleviating female urinary incontinence because of its proximity to the urethra 18 and is the location where a urinary incontinence device should be positioned. The middle third of the vaginal canal 26 is also horizontally offset from the symphysis pubis 22, which is a bony prominence situated adjacent to a front portion 38 of the human torso 10 and may be referred to the bladder neck region 50. Cooperation between a urinary incontinence device positioned in the vagina 12 and the symphysis pubis 22 allows the urethra 18 to be compressed upon itself thereby providing a means to alleviate involuntary urine flow from the bladder. Placement of the device high in the vaginal vault, near the cervix, allows for anatomical realignment of the bladder neck region, restoring the mechanism that allows for continence.

The urethra 18, also referred to as a urethral tube, is a hollow tubular structure that extends from a first opening 40 that exits the human body 10 to a second opening 42 situated at the lower surface of the bladder 20. The urethra 18 has a length of about 1.5 inches (about 38 mm) in most women. The urethra functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIG. 1, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) which transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

A urinary incontinence device 100 is shown positioned in the vaginal canal 26 and, in particular, in the bladder neck region 50 resting near the cervix 14. The urinary incontinence device 100 is designed to bridge across the vagina to support the musculature and body tissue located in the urethra-vaginal myofascial area 46. In other words, the device 100 elevates the bladder neck 50 to a more normal retropubic position thereby restoring continence.

In FIG. 2, one embodiment of the urinary incontinence device 100 is shown in use. A portion of the urinary incontinence device 100 and, in particular, a portion of the top 110 of the insert 102 is directly touching the anterior and posterior walls 34 and 36. Alternatively, the insert 102 can be selectively positioned such that a portion of the top 110 can be touching both the right and left lateral walls 30, 32 and the anterior and posterior walls 34, 36 to provide a supportive backdrop for the urethral tube 18 and to support the bladder neck region 50 thereby restoring continence. The urethral tube 18 can now be sufficiently compressed to intercept the flow of urine and to elevate and support the urinary sphincter muscle 44 so that it can function properly. By permitting the urethral tube 18 to be compressed upon itself between the urinary incontinence device 100 and the symphysis pubis 22, the involuntary flow of urine from the bladder is limited.

Figure 3:
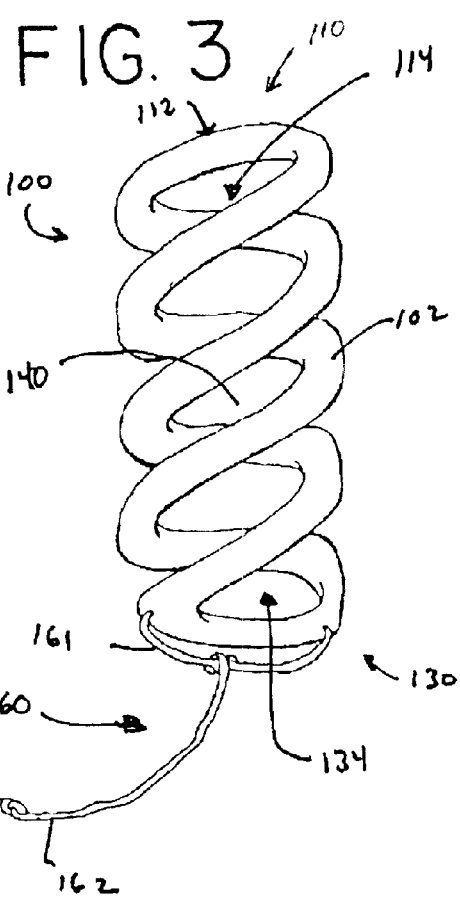
FIG. 3 is a front view of one embodiment of the urinary incontinence device of the present invention having a helical shape
Figure 4:
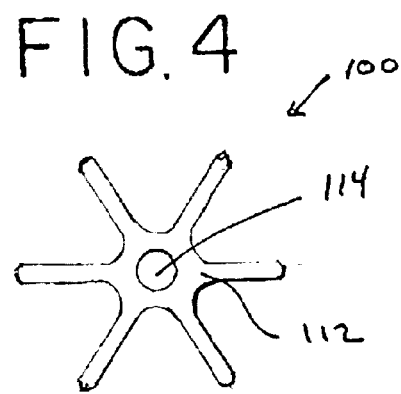
FIG. 4 is a top view of an alternative embodiment of the urinary incontinence device of the present invention having a pinwheel design and showing the device in an open state.
Figure 5:
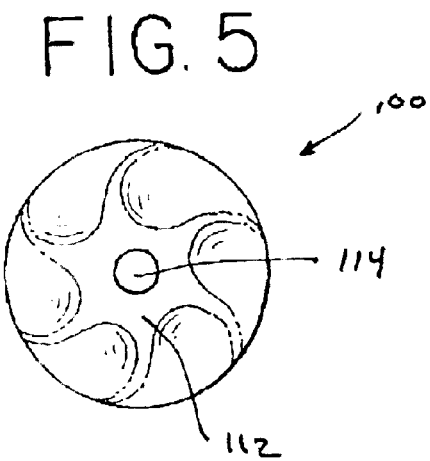
FIG. 5 is a top view of the urinary incontinence device of FIG. 4 showing the device as it might appear when contained in a carriage for an applicator system or after it has been inserted.

Referring now to FIG. 3, a front view of one embodiment of the device 100 of the present invention is shown. The device 100 includes an insert 102 having a top 110 with a top surface 112 and a bottom 130 with a bottom surface 132. In the embodiment shown in FIG. 3, the insert 102 is in the shape of a helix. In this regard, the top 110 includes a passage 114 that connects with a passage 134 provided on the bottom 130 through a channel 140 that allows fluids to pass through the insert 102.

It is desired that the shape of the insert 102 does not present any sharp corners or surfaces but instead is shaped to present rounded or curved surfaces to minimize any discomfort during use and removal of the device 100. Accordingly, in the embodiment shown in FIG. 3, the top 110 and bottom 130 have a round cross-section and, in particular, a substantially circular cross-section. Alternatively, the top 110 and bottom 130 may have an oblong or elliptical cross section.

The insert 102 may be formed from a variety of biocompatible materials and may be formed as a solid or a semi-solid mass of a compressible, resilient, biocompatible material such that the insert 102 deforms and substantially conforms to the shape of the portion of the object that is deforming the insert. In other words, the insert 102 is made from a material that will conform to the shape of the vaginal walls yet will provide sufficient support to the bladder neck region. Such biocompatible materials include, but are not limited to biocompatible plastics, silicones, polyurethane, and gels. One skilled in the art will understand that such compressible, resilient, biocompatible materials can be adjusted and/or tailored to provide a desired degree of compressibility and/or resiliency. In other words, the compressible, resilient biocompatible material can be adjusted and measured by a consumer perceived attribute of softness, pillowy, cushiony, and/or firmness and is in relationship with the desired level of support while maintaining an ability to conform to the shape of the vaginal walls and/or the cervical formices.

The device 100 may also be provided with a removal member 160 to facilitate the removal of the insert 102 from the vagina. The removal member 160 may be separate from the insert 102 or may be integrally formed with the insert 102. Preferably, the removal member 160 is connected to a portion of the bottom of the insert 130 (when referring to the position of the insert when it is in use).

The removal member 160 has a shape suitable for digital grasping so that the insert 102 may be removed. For example, FIGS. 3–5, and 9 show the removal member 160 as a combination of a loop 161 and a string 162. In these embodiments, the string 162 may be omitted and the removal member 160 may simply include the loop 161. Alternatively, as best seen in FIGS. 8 and 11, the loop 161 may be omitted and the removal member 160 may simply include a string 162.

In some embodiments, for example that shown in FIG. 3, when the insert 102 is grasped by removal member 160 and pulled in a downward direction, the insert 102 collapses into itself and elongates into a slender cylinder for easy comfortable removal.

The insert 102 may be made in a variety of suitable shapes as long as the insert has a top 110, a bottom 130, and is compressible and resilient such that the insert 102 deforms and substantially conforms to the shape of the object that deforms the insert 102 (e.g., the walls of the vagina). Alternative embodiments of the insert 102 according to the present invention are shown as FIGS. 4–11.

Referring to FIG. 8, the insert 102 is shown as formed of a thin wall 150 to define an outer surface 152 and an inner surface 154 where the inner surface 154 defines an interior of the insert 156. The thin wall 150 may have a thickness from about 0.025 mm to about 10 mm, preferably from about 1 mm to about 7 mm, more preferably about 2 mm. When the insert 102 is formed of a thin wall 150, the insert 102 may be formed as a single piece. It is to be understood that each of the inserts shown in the appended figures can be formed with the thin wall, as described above.

The interior of the insert 154 may be filled with a resilient material that allows the wall 150 and thus the insert 102 to conform to the shape of an object deforming the wall 150. The compressible, resilient material used to fill the interior 154 may include, but is not limited to, biocompatible fluids, mineral oil, silicone, saline, gels, clay, rubber, wool, fibrous material, semi-solid materials normal saline solution, aqueous gel, mineral gel, air or other gas, and mixtures thereof.

Referring now to FIG. 9, another embodiment of the present invention is shown where like reference numerals designate the same or similar parts as those shown in the other figures. In this embodiment, the thin wall 150 forming the insert 102 is a double wall structure that includes an outer wall 250 and an inner wall 260. The outer wall 250 defines an outer surface 252 and an inner surface 254. Likewise, the inner wall 260 defines an outer surface 262 and an inner surface 264. Together, the inner surface 254 and the outer surface 262 define a plenum 270.

The plenum 270 may be filled with compressible, resilient materials that include, but are not limited to biocompatible plastics, silicones, polyurethane, gels, normal saline solution, aqueous gel, mineral gel, air or other suitable compressible, resilient material that will allow the thin wall 150 and the outer wall 250 and inner wall 260 to conform to the shape of an object contacting and deforming the outer surface 252 of the outer wall 250. Other suitable compressible, resilient materials may include but are not limited to biocompatible fluids, mineral oil, clay, rubber, wool, fibrous material, semi-solid materials, and mixtures thereof. In addition, the interior 154 may be filled with a compressible, resilient material that is the same as or different from the compressible, resilient material that is present in the plenum. In addition, the plenum 270 and/or the interior 154 may include a medicament or drug for immediate or prolonged therapeutic effect.

The device 100 not including the removal member may have a length from about 10 mm to about 120 mm, suitably from about 30 mm to about 90 mm, more suitably from about 50 mm to about 70 mm and most suitably about 65 mm. The top 110 of the device 100 may also have a width across its widest dimension from about 10 mm to about 90 mm, suitably from about 30 mm to about 70 mm, more suitably from about 45 mm to about 65 mm. The bottom 130 of the device 100 may have the same or different width as the top 110. In general, however, the bottom will have a width across its widest dimension from about 10 mm to about 90 mm, suitably from about 30 mm to about 70 mm, more suitably from about 45 mm to about 65 mm.

Advantageously, the device 100 may be of a unitary construction and may be formed by molding an inert, biocompatible synthetic resin that has a modulus of elasticity. One such resin is a molded silicone compound, polyurethane, or other suitable biocompatible material or a combination of materials. As noted above, the device 100 may be formed of a solid or semi-sold resilient mass or may be formed with a thin wall. In any event, the device 100 whether made of unitary construction or otherwise, is made of a suitable biocompatible material, which is known to those of skill in the art. The device 100 may be covered with a suitable biocompatible outer cover material.

The device of the present invention as described above may be disposed after a single use, may be worn more than once, or may be reusable for a period of time (e.g., one month) before being disposed.

In accordance with another aspect of the invention, a method of instructing a consumer is provided. In this aspect, the method includes providing an insert to a user for alleviating female urinary incontinence and comprises the steps of providing a compressible resilient insert comprising a top and a bottom; and instructing the user to place the insert into a woman's vagina, wherein at least a portion of the top of the insert contacts one of an anterior vaginal wall, a posterior vaginal wall, an anterior cervical formix, or a posterior cervical formix.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. A vaginal urinary incontinence device comprising a compressible resilient insert having a top and a bottom such that when the insert is inserted within a vagina, at least a portion of the top deforms and substantially conforms to at feast one of an anterior vaginal wall, a posterior vaginal wall, an anterior cervical fornix, and a posterior cervical fornix, wherein the insert has a shape of a helix.

2. The device of claim 1 wherein the top has a substantially circular cross section.

3. The device of claim 1 further comprising a removal member located adjacent the bottom.

4. The device of claim 1 further comprising a thin wall to define an outer surface and an inner surface.

5. The device of claim 4 wherein the inner surface defines an interior of the insert.

6. The device of claim 5 further comprising a compressible resilient material within the interior of the insert to allow the wall to conform to a shape of an object deforming the wall.

7. The device of claim 4 wherein the thin wall is formed with an outer wall and an inner wall spaced from the outer wall to define a plenum.

8. The device of claim 7 wherein the plenum contains a compressible resilient material to allow the outer wall to conform to a shape of an object deforming the outer wall.

9. The device of claim 8 wherein at least one of the plenum or the interior includes a medicament or drug.

10. The device of claim 1 wherein the insert is a solid mass of compressible resilient material.

11. A vaginal urinary incontinence device comprising:

a. a compressible resilient insert in the shape of a helix and being formed from a biocompatible material selected from the group consisting of biocompatible plastics, silicones, polyurethanes, and gels, the insert having a top and a bottom such that when the insert is inserted within a vagina, at least a portion of the top deforms and substantially conforms to at least one of an anterior vaginal wall, a posterior vaginal wall, an anterior cervical fornix, and a posterior cervical fornix; and b. a removal member located adjacent the bottom.

12. The device of claim 11 wherein the insert further comprises a thin wall to define an outer surface and an inner surface.

13. The device of claim 12 wherein the inner surface defines an interior of the insert.

14. The device of claim 13 further comprising a compressible resilient material within the interior of the insert to allow the wall to conform to a shape of an object deforming the wall.

15. The device of claim 14 wherein the thin wall is formed with an outer wall and an inner wall spaced from the outer wall to define a plenum.

16. The device of claim 15 wherein the plenum contains a compressible resilient material to allow the outer wall to conform to a shape of an object deforming the outer wall.

17. The device of claim 16 wherein at least one of the plenum or the interior includes a medicament or drug.

18. A method of providing an insert to a user for alleviating female urinary incontinence comprising the steps of:

a. providing an insert comprising a top and a bottom in the shape of a helix, wherein the insert is formed from a biocompatible material selected from the group consisting of biocompatible plastics, silicones, polyurethanes, and gels; and b. instructing the user to place the insert into a woman's vagina, wherein at least a portion of the top deforms and substantially conforms to at least one of an anterior vaginal wall, a posterior vaginal wall, an anterior cervical fornix, and a posterior cervical fornix.

19. The method of claim 18 further comprising removing the insert from the vagina.

20. The method of claim 18 further comprising pulling the insert from an end, wherein the insert further comprises a thin wall to define an outer surface and an inner surface, wherein the inner surface defines an interior of the insert having a compressible resilient material within the interior of the insert to allow the wall to conform to a shape of an object deforming the wall and wherein the insert collapses to form a slender cylinder when the insert is pulled from an end.

21. A vaginal urinary incontinence device comprising a compressible resilient insert having a top and a bottom such that when the insert is inserted within a vagina, at least a portion of the top deforms and substantially conforms to at least one of an anterior vaginal wall, a posterior vaginal wall, an anterior cervical fornix, and a posterior cervical fornix, wherein the insert comprises a thin wall to define an outer surface and an inner surface and wherein the thin wall is formed with an outer wall and an inner wall spaced from the outer wall to define a plenum.

* * * * *